United States Patent [19]

Makiguchi et al.

[11] Patent Number: 4,778,763

[45] Date of Patent: Oct. 18, 1988

[54] ANALYTICAL METHOD AND APPARATUS FOR DETERMINING FLUORESCENCE OR PHOSPHORESCENCE

[75] Inventors: Kyoko Makiguchi, Katsuta; Yasushi Nomura, Mito, both of Japan

[73] Assignee: Hitachi, Ltd., Tokyo, Japan

[21] Appl. No.: 853,969

[22] Filed: Apr. 21, 1986

[30] Foreign Application Priority Data

Apr. 19, 1985 [JP] Japan ................................. 60-82424

[51] Int. Cl.[4] ...................... G01N 21/64; G01N 35/02
[52] U.S. Cl. .................................... 436/47; 250/459.1;
422/64; 422/65; 422/67; 422/52; 436/172
[58] Field of Search .................. 250/302, 459.1, 461.1;
436/172, 800, 805, 825, 47; 435/7; 422/64, 65, 67, 52

[56] References Cited

U.S. PATENT DOCUMENTS

| | | | |
|---|---|---|---|
| 4,198,567 | 4/1980 | Eneroth et al. | 250/459.1 |
| 4,239,964 | 12/1980 | Robbins et al. | 250/461.1 X |
| 4,313,735 | 2/1982 | Yamashita et al. | 422/67 X |
| 4,365,153 | 12/1982 | Seigel et al. | 250/461.1 X |
| 4,407,964 | 10/1983 | Elings et al. | 436/518 |
| 4,438,329 | 3/1984 | Ford et al. | 250/459.1 |
| 4,485,308 | 11/1984 | Rabatin | 250/461.1 |

FOREIGN PATENT DOCUMENTS 59-24380 8/1984 Japan .

Primary Examiner—Michael S. Marcus
Attorney, Agent, or Firm—Antonelli, Terry & Wands

[57] ABSTRACT

A turntable holding a train of reaction containers thereon is continuously turned by one revolution plus an angle for a share of one container and then stopped. This makes one cycle. On the route of transfer of the reaction container, there are provided a light irradiation position and a light collection position.

The reaction container into which a sample and a marker reagent have been introduced is transferred such that it does not stop at the irradiation position and the light collection position. The reaction container to which a monochromatic light for excitation has been irradiated at the irradiation position is transferred toward the light collection position. Fluorescence coming from the light collection position is lead to a photodetector, and the concentration of the target substance in the sample is determined from the detected fluorescence after arithmetic processing.

Since the light collection position is provided at a place different from the irradiation position in the present apparatus, it is possible to measure fluorescence originating from the sample which is substantially free from the influence of background fluorescence.

11 Claims, 4 Drawing Sheets

F I G. 3
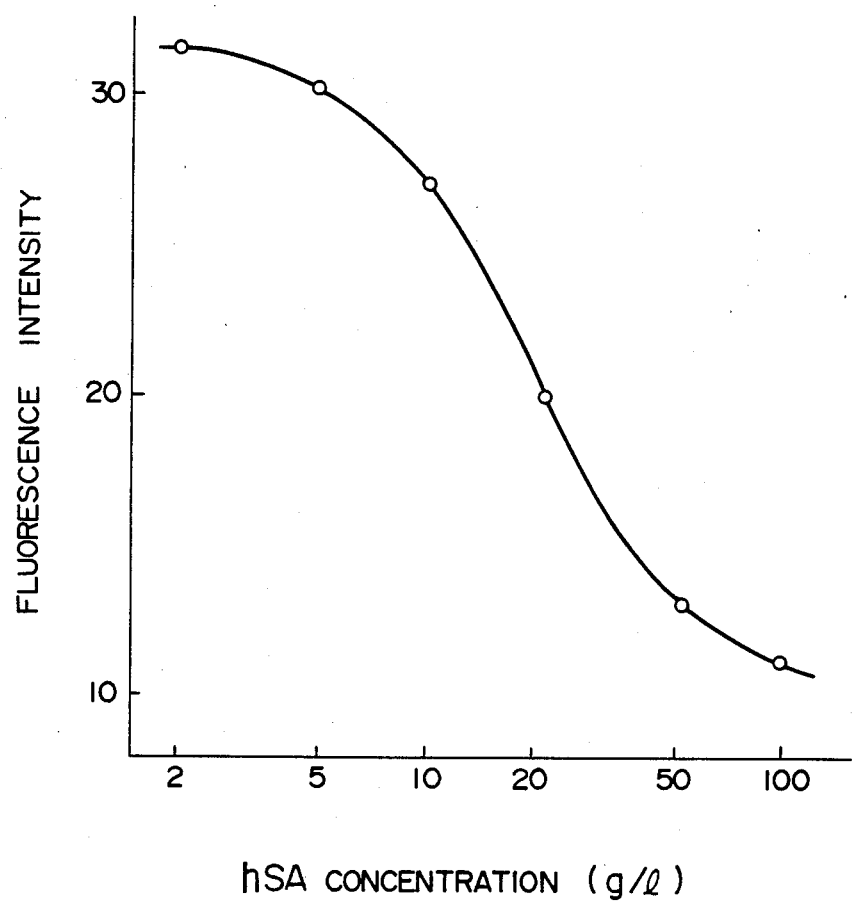

ANALYTICAL METHOD AND APPARATUS FOR DETERMINING FLUORESCENCE OR FLUORESCENCE

BACKGROUND OF THE INVENTION

This invention relates to an analytical method and an analytical apparatus for determining fluorescence or phosphorescence. More particularly, it relates to a method and an apparatus suitable for allowing a sample to react in a cuvette or a reaction container and then determining fluorescence or phosphorescence resulting from the reaction.

In recent years, there has been a strong demand in the field of medical treatment for quantitative determination of a very small amount of substances. There have already been devised various methods of quantitatively determining substances in body fluids by immunological technique, namely by utilizing antigen-antibody reactions. For example, there have been known methods of measuring the sedimentation or the agglomeration of reactants, such as the capillary sedimentation method, immunoturbidimetry, immunonepherometry and the latex agglomeration method, and labelled immunoassay using labelling substances such as enzymes, radioisotopes or fluorescent substances. Among these methods of determination, labelled immunoassay is attracting attention owing to such factors as high sensitivity in determination and ease in handling the necessary reagents. Labelled immunoassays include those of a homogeneous reaction system (homogeneous immunoassay) and those of a heterogeneous reactio system (heterogeneous immunoassay). A homogeneous reaction system is a system in which the separation of a marker substance bound to the reaction product of an antigen and an antibody (B: BOUND) from the marker substance present in the free state (F: FREE), namely B/F separation, is unnecessary and the determination can be conducted while the above two are in a mixed state, whereas a heterogeneous reaction system is a system in which the two are first separated from each other and then the label amount of either of the two is determined.

When the concentration of a target substance in sample is determined by a fluorescently labelled method using a homogeneous reaction system, there arises a problem of blank fluorescence. This point will be explained a little more in detail below.

Conventional fluorophotometers basically consist of five parts of a light source, an excitation wavelength selector such as a monochromator, a sample chamber, an emission wavelength selector or a monochromator, and a photodetector. Thus, a light radiated from a light source is separated into its spectral components through an excitation wavelength selector and then irradiated to a sample. The resulting fluorescence is taken out from a direction perpendicular to the direction of irradiated light, passed through a fluorescence wavelength selector, and then received by a detector. The light arriving at the detector has much possibility of being contaminated with other components than the fluorescence originating from fluorescent molecules. These superfluous lights are called blank fluorescence. Conceivable causes of blank fluorescence include scattered or reflected light, Raman scattering light from solvents, fluorescence from solvents and fluorescence cells, the secondary light of scattered or reflected light, and a component of abnormal reflection occurring in the optical system including a spectroscope.

It is needless to say that when the fluorescent sample is in a substantially high concentration the intensity of these blank fluorescence components becomes relatively weak. However, when the concentration is extremely low (for instance, in the determination of ultramicroquantity components) or when the sample in turbid, the influence of the blank fluorescence components on the determination of the fluorescence component originally intended is large and cannot be neglected. Further, fluorescence originating from the contaminants in the sample also causes an error in determination. Blank fluorescence components which appear at the same wavelength as that of exciting light come mainly from light scattered by solvent molecules as Reyleigh scattering.

Further, the proteinous reactant in an agglomerated state formed as the result of an antigen-antibody reaction appears itself in a high concentration and inevitably causes the increase of scattered light. When the resolving power of the spectroscope is poor, the bottom of the scattered light component extends toward long wavelength side and overlaps extensively with the fluorescence emission region. Although this problem is somewhat alleviated when the slit width of the spectroscope is reduced in determination, then the detected intensity of fluorescence is also reduced and a determination of high accuracy cannot be expected.

A method of decreasing the influence of blank fluorescence is disclosed, for example, in U.S. Pat. No. 4,421,860. In the disclosed method, fluorescence resulting from a free, fluorescently-labelled reactant on one hand and fluorescence resulting from the fluorescently labelled reactant bound to giant particles on the other hand can be determined separately from each other; however, since the sample is not moved as to its position, this method is not suited to continuous analysis.

Blank fluorescence and fluorescence originating from contaminating components are hereinafter referred to collectively as background fluorescence.

SUMMARY OF THE INVENTION

An object of this invention is to provide an analytical method and an analytical apparatus which enable an efficient determination of fluorescence or phosphorescence originating from a sample.

Another object of this invention is to provide an analytical method and an analytical apparatus which enable a determination to be conducted with a small error by reducing the influence of background fluorescence.

The method according to this invention comprises introducing a sample and a marker reagent into a movable reaction container; transferring the cuvette into which the marker reagent has been introduced to an irradiation position and irradiating to the cuvette an exciting light; and transferring the cuvette to which the exciting light has been irradiated to a light taking-out position and detecting fluorescence or phosphorescence originating from the sample in the cuvette.

Another aspect of the present invention includes an analytical apparatus comprising an exciting light irradiation position provided on the locus of transfer of reaction containers; a light taking-out position provided on the said locus of transfer of reaction containers and away from the said irraiation position; means to transfer the reaction containers having a sample therein such that the containers pass through the said irradiation position and the light taking-out position; means to direct the exciting light toward the said irradiation position; and means to detect fluorescence or phosphorescence originating from the sample in the reaction container coming from the said light taking-out position.

A preferred embodiment of this invention is constructed such that there is introduced into a movable reaction container a marker reagent which will emit a fluorescence having a longer life than the time necessary for the reaction container to move from the above-mentioned irradiation position to the above-mentioned light collection position, and the concentration of the target substance in the sample is calculated based on the value measured with the above-mentioned detector. Further, in a preferred embodiment, the irradiation position and the light collection position are provided on the transfer route of the train of reaction containers on a turntable, and fluorescence or phosphorescence is taken out from a position different from the irradiation position, so that the photodetector needs not be provided in the direction perpendicular to that of incident beam. Consequently, the condition of arranging the photodetector becomes favorable to the automization of analytical apparatuses.

In a preferred embodiment of this invention, the photometry of fluorescence can be conducted while the train of reaction containers is kept moving, so that the reaction containers need not be kept stopping during irradiation and photometry.

Further, in a preferred embodiment, the light source, the photodetector, and a device for transferring reaction containers are so arranged as to enable the light beam to pass through the reaction container plural times and the state of the reaction solution to be observed plural times; plural reagents are introduced with a time difference; the amount of light resulting from each of the reactions is measured and the data thus obtained are arithmetically processed, whereby the light amount other than that originating from the intended reaction is subtracted and the concentration of the target substance can be calculated.

BRIEF DESCRIPTION OF THE DRAWINGS

FIGS. 3 and 4 are graphs illustrating examples of a working curve for human serum albumin (hereinafter referred to as hSA).

DETAILED DESCRIPTION OF THE PREFERRED EMBODIMENT

Figure 1:
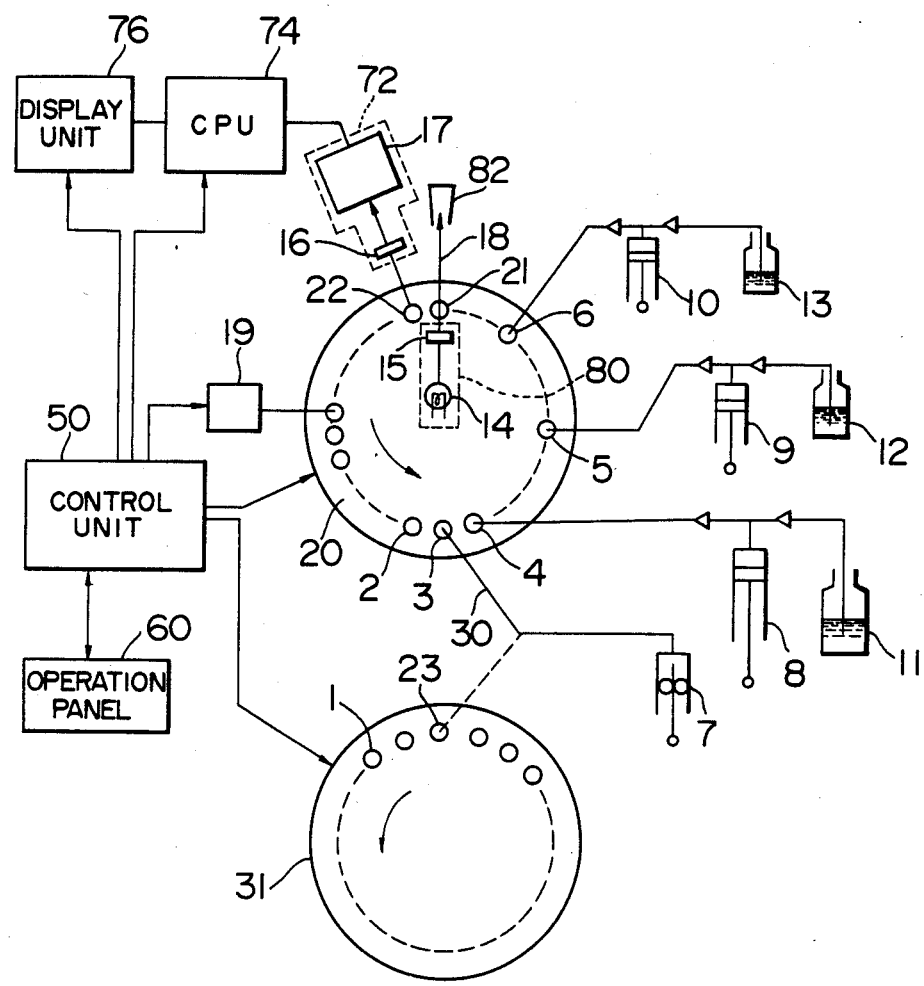
FIG. 1 is a diagram showing the outline of the structure of one working example of this invention.

FIG. 1 shows the outline of the structure of one working example of this invention. In this example, the reaction line has a reaction disc 20 in the form of a turntable on which a number of reaction containers are disposed on a concentric circle, in order to meet the requirement of multi-item simultaneous analysis and discrete system. On the disc 20 are provided a specimen dispensing position and two or more reagent dispensing positions. In the vicinity of the disc, there is provided a reaction detector for detecting the reaction occurring in the reaction container. The reaction disc is rotated such that the train of reaction containers through which light beam has been passed goes past before the reaction detector, whereby the reaction can be detected.

The rotation of the reaction disc 20 can be controlled according to said means to transfer the reaction containers such as, for example, the one described in U.S. Pat. No. 4,313,735. Thus, rotational transfer and stoppage are conducted every one cycle by means of a control unit 50. The angle of rotation in one cycle is set at 360 degrees plus one pitch of the reaction container. The sample is reacted with the first reagent, the second reagent, and the third reagent, and the reactions are measured every one cycle to determine the target component in the sample quantitatively. Thus, plural reagents are introduced with a time difference, each of the reactions is measured, and the reaction data obtained are arithmetically processed, whereby the background fluorescence originating from the sample itself can be compensated and the intended sample component can be determined quantitatively.

In FIG. 1, the reaction disc 20 holds along its circumference a train of plural cuvettes or reaction containers 2 which serve also as measuring cells. The velocity of the reaction disc can be selected in plural stages in accordance with the nature of samples. The reagents is dispensed by means of dispensers 8, 9 and 10. A typical example of said means to detect fluorescence or phosphorescence originating from the sample in the reaction container can be a multi-wavelength photometer 72 which comprises a wavelength selector 16 and a photodetector 17. But it has no lamp. The wavelength selector 16 comprises a concave grating, and the photodetector 17 comprises a photo-diode array of semiconductors. A typical example of said means to direct the exciting light toward the said irradiation position can be an exciting light production unit 80 comprising a light source lamp 14 and a device for taking out monochromatic light, for example an optical filter 15. Light 18 from the exciting light production unit 80 goes through the irradiation position 21 and is directed toward an optical trap 82.

Many modifications and rearrangements as to said means and said positions of the present invention can of course be carried out without departing from the scope thereof.

On the locus of the transfer of the reaction container train, namely on the route of transfer, there are provided reagent introduction positions 4, 5 and 6, an irradiation position 21, and a light taking-out position or light collection position 22. The light taking-out position 22 is provided at a place distant from the irradiation position 21 in order to avoid the influence of the exciting light.

When the reaction disc is rotating, the train of reaction containers 2 to which the reagents have been introduced goes through the irradiation position 21 and then through the light collection position 22. At the irradiation position 21, the train traverses the beam 18 of exciting light which has been emitted from the light source 14 and made monochromatic with the optical filter 15. The sample in the reaction container is excited by the exciting light to emit fluorescence, which is then directed from the light collection position 22 to the photodetector 17. The detection signal obtained in the multiwavelength photometer 72 is processed in a processing unit 74 (hereinafter referred to as CPU), and the concentration of the target substance in the sample is displayed on a display unit 76. The conditions of measurement are instructed by the operator through an operation panel 60 to the control unit 50.

The distance between the irradiation position 21 and the light collection position 22 is in close connection with the rotational velocity of the reaction disc 20. The light collection position is not restricted to a single place, and plural such positions may be provided along the route of transfer of reaction containers to select the period of time elapsing from excitation till fluorescence photometry. However, FIG. 1 shows solely an example of a single such position.

The time from excitation till fluorescence photometry is related with the life of fluorescence or phosphorescence caused by a fluorescent or phosphorescent substance used as the marker, and with the rotational velocity of the reacion disc 20. Here, the time from the irradiation of the exciting light to the reaction sample till the photodetection is set so as to be longer than the life of background fluorescence originating from contaminants and shorter than the life of fluorescence due to the labelling substance used as the marker. Thus, the reaction disc 20 rotates at a velocity which enables the reaction container to move from the position 21, where the light beam passed through the container, till the photodetection position 22 in a period of time shorter than the life of fluorescence or phosphorescence.

The operations of the analytical apparatus will be explained further in detail. When a sample container 1 containing a sample to be measured (for example, serum) on the sample table 31 comes to a sampling position 23, a prescribed amount of the serum is sucked into a sampling probe 30 and then discharged into a reaction container 2 which has been transferred to a discharge position 3. After completion of the sampling operation, the reaction disc 20 rotates anti-clockwise by an angle of 360 degrees plus one pitch of the reaction container and then stops. During the above rotation of the reaction disc, all of the reaction containers on the reaction disc pass through the beam 18. Accordingly, after the passage of respective reaction containers through the beam 18, fluorescence or phosphorescence develops in the reaction solution. The fluorescence or phosphorescence is detected with a photodetector 17 provided at a position deviated from the beam 18, to determine the light intensity.

When the time during which the reaction disc 20 is rotating and is stopping as mentioned above is assumed to be 20 seconds in all, the above-mentioned operations will be repeated with a cycle time of 20 seconds. Thus, a particular specimen once sampled will advance its position on the reaction disc in the stopped state by one pitch of the reaction container anticlockwise as the above-mentioned cycles proceed.

At positions 4, 5 and 6, which correspond, for example, to the advance of the position on the reaction disc in the stopped state of 1, 10, and 20 pitches of the reaction container, respectively, there are provided the reagent supply nozzle of dispensers 8, 9 and 10, respectively, to discharge the reagent necessary for the reaction. The first reaction proceeds by the action of the first reagent 11 added with the first dispenser 8, and the course of the reaction until the addition of the second reagent 12 is measured with 20 seconds as one cycle. Similarly, the second and the third reaction which proceed by the action of the second and the third reagent 12 and 13 added with the second and the third dispenser, 9 and 12, respectively, are also measured with 20 seconds as one cycle. Fluorescence or phosphorescence intensity is determined based on the measured values obtained above and compared with a working curve prepared beforehand, whereby the quantity of the target substance in the specimen is determined.

According to this working example, since the optical path of the photodetector 17 is provided at a position 22 which is away from the position opposite to the light source lamp 14, the desired intensity of fluorescence or phosphorescence can be determined without being affected by scattered light and the like resulting from exciting light. In FIG. 1, 7 is a pipetting device for sucking a sample into a sampling probe 30 and discharging the sample held therein, and 19 is a washing mechanism for washing the reaction container for reuse.

Figure 2:
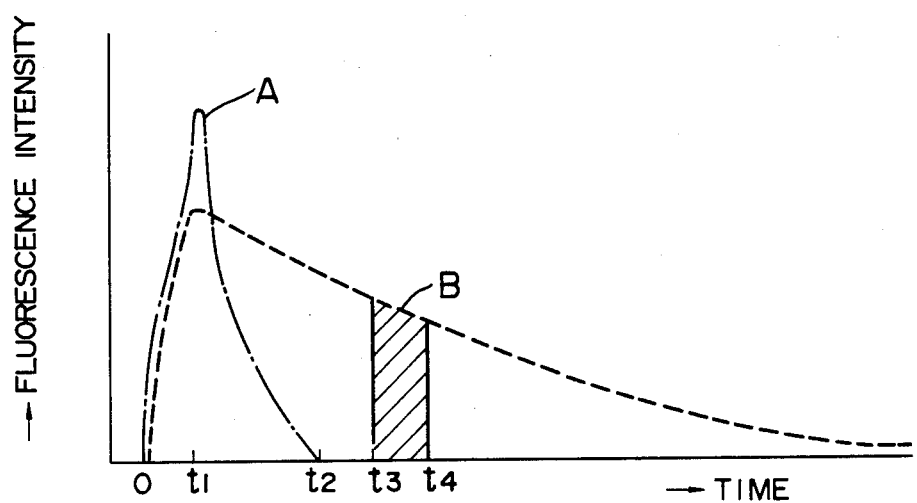
FIG. 2 is a graph to illustrate the timing of photometry in the example shown in FIG. 1.

The influence of background fluorescence in the sample can be eliminated by controlling the time from the irradiation of exciting light to the sample reaction liquid until the photodetection. FIG. 2 shows a schematic diagram illustrating the timing of photometry in the automatic analytical apparatus shown in FIG. 1. Light beam 18 is irradiated to the sample reaction liquid from the time when the reaction container arrives at the irradiation position until it passes through the position, namely from time 0 till $t_1$. The irradiation of the exciting light causes the excitation of the fluorescent substance added to the reaction liquid as a reagent, and the intensity of fluorescence originating from the sample exhibits a change with elapsed time after the irradiation as shown by curve B. Various contaminants present in the sample also emit fluorescence by the irradiation of from time 0 to time $t_1$. The resulting background fluorescence exhibits a change of intensity with time as shown by curve A.

The life of the labelling substance used as the reagent for automatic analysis in this example is longer than the life $t_2$ of background fluorescence. In the example, an amount of fluorescence is detected which corresponds to time interval of from $t_3$ to $t_4$ as shown by oblique lines in FIG. 2. Thus, the rotational velocity of the reaction disc 20 is controlled such that the reaction container which passed the beam-passing position 21 reaches the light collection position 22 at time $t_3$. The fluorescence emitted from the sample reaction liquid in the reaction container which reached the light collection position 22 is taken into the photodetector 17 from time $t_3$ till an appropriate time $t_4$ to be used in arithmetic processing.

EXPERIMENTAL EXAMPLE

This example is to show the results of determination of hSA conducted on the apparatus shown in FIG. 1. Solutions of following compositions were used as examples of reagent compositions preferable in this case.

The first reagent: hSA labelled with IAA-eosine (eosine-5-iodoacetate amide)
The second reagent: anti-hSA serum of 40-fold dilution
The third reagent: anti-IAA-eosine serum of 200-fold dilution The conditions of reaction and determination are as follows:
Amount of sample: 100 μl of a sample of 400-fold dilution
Amount of the first reagent: 500 μl
Amount of the second reagent: 500 μl
Amount of the third reagent: 500 μl
Excitation wave length: 500 nm
Fluorescence wavelength: 570 nm A specimen containing a target component is set on the sample table 31, and the first, the second, and the third reagents are placed in the dispensers. Upon the instruction of the start of analysis, the apparatus operates according to the working principle described above. The reaction in the reaction container 2 can be traced as follows. When the sample, the first reagent, and the second reagent are mixed together, the sample (hSA) and the IAA-eosine-labelled hSA react with anti-hSA antibody in competition with each other. When the third reagent is subsequently added to the reaction liquid, free IAA-eosine-labelled hSA reacts with anti-IAA-eosine antibody to undergo quenching, whereas IAA-eosine-labelled hSA which has reacted with anti-hSA antibody does not react with anti-IAA-eosine antibody because of steric hindrance and hence can emit a light. Since the amount of the light is in definite relation to the concentration of hSA in the sample, the hSA concentration in the sample can be determined by measuring the light amount and comparing it with a working curve prepared beforehand.

In this Experimental Example, the life ($\tau$) of the reaction product between luminescent IAA-eosine-labelled hSA and anti-hSA antibody is 1 m sec, whereas that of background fluorescence originating from contaminants usually contained in serum is in the order of n sec to $\mu$ sec. The transfer velocity of the reaction container was set at $3.9 \times 10^4$ mm/sec, so that the photodetector was disposed at a position 20 mm away from the light beam, and the photodetection was conducted for 0.1 m sec.

FIG. 3 shows the working curve used in this determination example.

Figure 4:
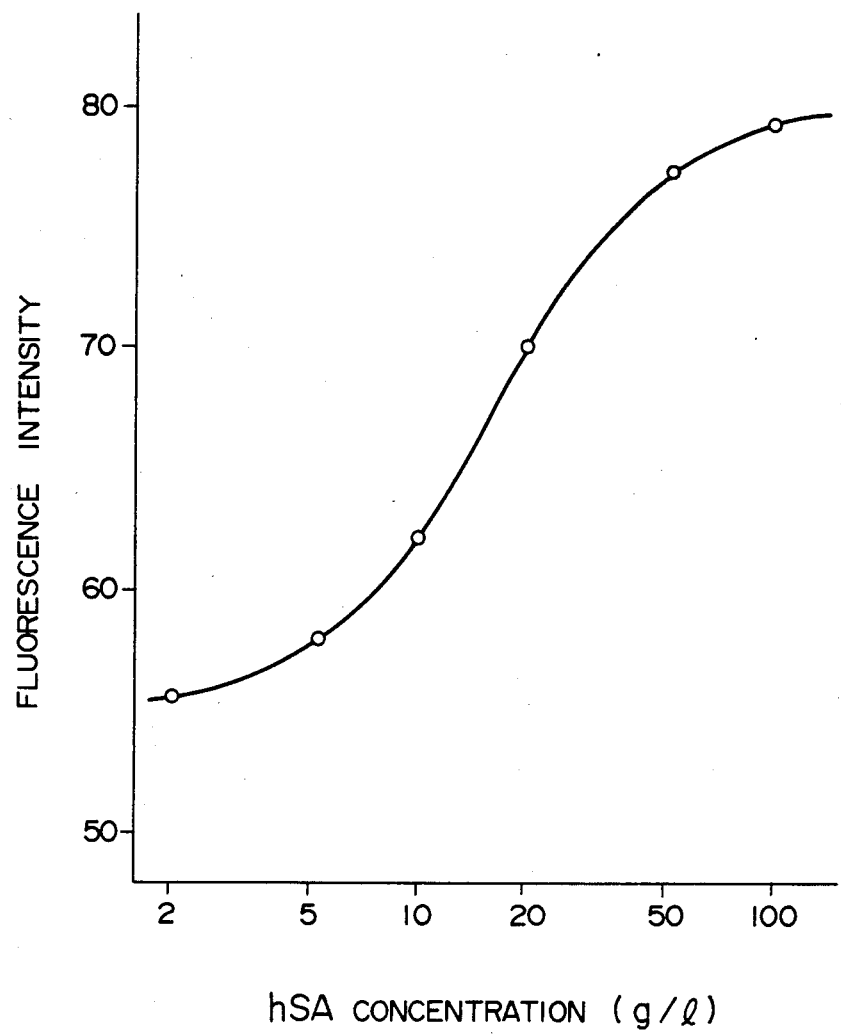

Further, in the above-mentioned Experimental Example, the light amount obtained after a prescribed time of reaction following the addition of the third reagent was subtracted from that before the addition of the third reagent, and the quantity of the target substance in the sample was determined based on the data thus obtained. The working curve for this case is shown in FIG. 4. Such subtraction can further reduce the determination error caused by light not directly originating from the reaction, such as that originating from the sample and the solvent used.

As the fluorescently labelled method using a homogeneous reaction system described above, there may be used polarization fluoroimmunoassay and quenching fluoroimmunoassay. Polarization fluoroimmunoassay is based on the principle that when an antigen labelled with a fluorescent substance is bound to a corresponding antibody, the size of the resulting molecule becomes very large, the rotational Brownian motion of the fluorescent molecule is suppressed, and the degree of polarization is increased as compared with that before the binding of the antibody. A smaller molecular weight of a fluorescently labelled antigen results in a larger difference between the Brownian motion before the binding to the antibody and that after the binding, giving a higher sensitivity. Accordingly, although the assay is widely used in the determination of haptens including medicines of a small molecule, it is difficultly used in the determination of target substances of a large molecule such as protein because then the difference in Brownian motion before and after the binding to an anti-body is small. On the other hand, quenching fluoroimmunoassay utilizes the quenching of fluorescence caused by the binding of a fluorescently labelled antigen to an antibody. Although the reaction mechanism is not yet clear, it is generally believed that the quenching is presumably due to the presence of an electron donor in the neighborhood of the antibody to which the antigen has tightly attached. According to this method, it is possible to determine both a proteinour target substance of a large molecular weight and a target substance of a small molecular weight like hapten.

In the working example described above, a highly sensitive analysis becomes possible in the quantitative determination of a target substance in a sample based on the measurement of delayed fluorescence or phosphorescence, since the influence of blank fluorescence or background fluorescence can be eliminated. The error in determination due to so-called background fluorescence originating from contaminants such as bilirubin contained in samples from patients can be avoided by using as the labelling substance a substance which emits a fluorescence or a phosphorescence having a longer life as compared with background fluorescence. Thus, the influence of background can be removed by measuring fluorescence or phosphorescence originating from a target substance at a time when a sufficient time has elapsed from the irradiation of exciting light to the reaction sample and the fluorescence resulting from contaminants has decayed.

As described in the foregoing, according to this invention, fluorescence or phosphorescence resulting from the reaction of the sample can be measured while the reaction containers are being transferred and hence efficient analytical operations are possible which are suited to automatization.

What is claimed is:

1. An analytical apparatus comprising:
   means for repeating alternate transfer and stoppage of a train of light-permeable reaction containers along a transfer path having a plurality of positions spaced apart from one another therealong, the plurality of spaced apart positions incuding a first position in which a reagent is added into at least a specified one of a train of reaction containers, a second position in which an exciting light irradiates a reactant solution contained in the specified one of the train of reaction containers, and a third position in which an emitted fluorescence or phosphorescence generated from the reactant solution contained in the specified one of the train of reaction containers irradiated by an exciting light at the second position is taken out, the transfer and stoppage means enabling the stoppage of another one of the train of reaction containers at the first position of the transfer path after the specified one of the train of reaction containers has been stopped at the first position;
   exciting light means provided at one side of the transfer path for generating and irradiating exciting light to the second position of the transfer path;
   means for detecting emitted fluorescence or phosphorescence generated from the reactant solution in the specified one of the train of reaction containers at the third position and providing a signal indicative thereof, the detecting means being provided at another side of the transfer path, the third position being spaced apart from the second position so that exciting light irradiated toward the second position is not received at the third position;
   means for adding a reagent containing at least one substance capable of emitting a fluorescence or phosphorescence by irradiation of the exciting light to at least the specified one of the train of reaction containers stopped at the first position, the reagent after addition to the specified one of the train of reaction vessels being subjected to reaction with a substance to be determined contained in a sample provided in the specified one of the train of reaction container; and means for processing the signal from the detecting means for determining the concentration of the substance to be determined;

wherein the transfer and stoppage means enables movement of the specified one of the train of reaction containers from the second position to the third position over a period of time longer than the lifetime of background fluorescence originated from contaminants contained in the sample contained in the specified one of the train of reaction containers.

2. An apparatus according to claim 1, wherein the means for transfer and stoppage includes means for transferring at least the specified one of the train of reaction containers through both the second and third positions without stoppage during the course of transfer along the transfer path.

3. An apparatus according to claim 1, wherein the transfer path is a closed path of movement and the train of reaction containers are arranged for transfer along the closed path of movement, the train of reaction containers being disposed on a reaction disc in the form of a turntable for rotation along the closed path of movement, the exciting light means being disposed at an inner side of the closed path of movement, the detecting means being provided at an outer side of the closed path of movement, the exciting light means irradiating exciting light at the second position through one side of a wall of the train of reaction containers, and the detecting means being arranged for detecting emitted fluorescence or phosphorescence from the reaction solution in the specified one of the train of reaction containers at the third position taken out through another side of the wall of the specified one of the train of reaction containers.

4. An apparatus according to claim 3, wherein the closed path of movement is a circular path of movement.

5. An apparatus according to claim 1, further comprising means disposed proximate to the transfer path for supplying a sample to a reaction container at each stoppage of the train of reaction of containers, and the means for adding a reagent being provided so as to add three types of reagent solutions into the same reaction container at different reagent adding positions along the transfer path.

6. An apparatus according to claim 2, wherein the transfer path is a closed path of movement and the train of reaction containers are arranged for transfer along the closed path of movement, the train of reaction containers being disposed on a reaction disc in the form of a turntable for rotation along the closed path of movement, the exciting light means being disposed at an inner side of the closed path of movement the detecting means being provided at an outer side of the closed path of movement, the exciting light means irradiating exciting light at the second position through one side of a wall of the train of reaction containers, and the detecting means being arranged for detecting emitted fluorescence or phosphorescence from the reaction solution in the specified one of the train of reaction containers at the third position taken out through another side of the wall of the train of reaction containers.

7. An apparatus according to claim 6, wherein the closed path of movement is a circular path of movement.

8. An apparatus according to claim 2, further comprising means disposed proximate to the transfer path for supplying a sample to a reaction container at each stoppage of the train of reaction of containers, and the means for adding a reagent being provided so as to add three type of reagent solutions into the same reaction container at different reagent adding positions along the transfer path.

9. An analytical method comprising the steps of:
repeating a cycle of alternate transfer and stoppage of a train of light-permeable reaction containers along a transfer path;

adding a sample containing a substance to be determined to a specified one of the train of reaction containers during the stoppage thereof at a first position along the transfer path while adding a reagent containing a reactant labelled with a substance capable of emitting a fluorescence or phosphorescence to another one of the train of reaction containers at a second position along the transfer path spaced apart from the first position during stoppage of the train of the reaction containers, the reactant being related to an immunological reaction, the reagent containing the reactant being added to the specified one of the train of reaction containers containing the sample during one of the cycles of transfer and stoppage of the train of reaction containers;

causing an immunological reaction derived from the presence of the substance to be determined in at least the specified one of the reaction containers containing the reactant and the sample therein;

generating a beam of exciting light at a third position spaced apart from the first and second positions along the transfer path and moving the train of reaction containers so as to traverse the beam of exciting light at the second position to enable fluorescence or phosphorescence to be emitted from a resulting reaction product of the sample and reagent as a result of an immunological reaction;

moving the train of reaction containers along the transfer path to a fourth position spaced apart from the third position in which the reaction container traversed the beam of exciting light, the train of reaction containers including the specified one of the train of reaction containers containing the reaction product from which an emission of a fluorescence or phosphorescence is enabled while the train of reaction containers is moving; and detecting emitted fluorescence or phosphorescence taken out at the fourth position for determining the concentration of the substance to be determined in accordance with the intensity of the fluorescence or phosphorescence detected;

wherein the specified one of the train of reaction containers is moved from the third position at which the specified one of the train of reaction containers traverses the exciting light beam to the fourth position over a period of time longer than the lifetime of background fluorescence originated from contaminants contained in the sample contained in the specified one of the train of reaction containers.

10. A method according to claim 9, wherein the transfer path is a circular closed path of movement and the step of irradiating the train of reaction containers with an exciting light includes providing an exciting light source at an inner side of the closed circular path of movement and the step of detecting emitted fluorescence or phosphorescence includes providing detection means at an outer side of the closed circular path of movement, the detection means being arranged so as to not receive exciting light from the exciting light source.

11. An analytical method comprising the steps of:
(a) adding a liquid sample containing an antigen into a specified one of a train of reaction containers movable along a transfer path having a plurality of spaced apart positions including reagent adding positions in which respective reagents are added to the reaction container, an irradiating position in which an exciting light irradiates a sample contained in the reaction container and a detecting position in which light emitted from a reactant solution in the reaction container is taken out;
(b) moving and stopping the reaction container at a first reagent adding position and adding a first reagent into the reaction container after movement thereof along the transfer path, the first reagent containing a marker comprising a substance classified as a cognate antigen of an antigen to be detected, and capable of emitting a fluorescence of phosphorescence;
(c) moving and stopping the reaction container at a second reagent adding position and adding a second reagent into the reaction container after movement from the first reagent adding position, the second reagent containing a cognate antibody of the antigen to be determined into the reaction container;
(d) moving and stopping the reaction container at a third reagent adding position and adding a third reagent into the reaction container after movement from the second reagent adding position, the third reagent comprising a substance having a capability of bonding with a labelled antigen which still remains free after the addition of the second reagent at the step (c) into the reaction container;
(e) moving the reaction container through the irradiating position in which an exciting light irradiates a reactant solution in the reaction container, and through the detecting position in which an emitted light from the reactant solution is taken out;
(f) irradiating the reactant solution in the reaction container with the exciting light at the irradiating position so that light of a fluorescence or phosphorscence is emitted from a resulting reaction product formed by a reaction between the labelled antigen and the cognate antibody; and
(g) detecting the fluorescence or phosphorescence emitted at the detecting position in which emitted light is taken out while the reaction container is moving;
wherein the step of moving the reaction container through the irradiating position and through the detecting position includes moving the reaction container from the irradiating position to the detecting position over a period of time longer than the lifetime of background fluorescence originated from contaminants contained in the sample contained in the reaction container.

* * * * *